(12) United States Patent
Kurer

(10) Patent No.: US 6,923,650 B2
(45) Date of Patent: Aug. 2, 2005

(54) GUIDE POST FOR TREPHINE

(76) Inventor: Hans Gustav Kurer, 106 Houghton Lane, Swinton, Manchester (GB), M27 0BT ( * ) Notice: Subject to any disclaimer, the term of this patent is extended or adjusted under 35 U.S.C. 154(b) by 0 days.

(21) Appl. No.: 10/220,532

(22) PCT Filed: Feb. 27, 2001

(86) PCT No.: PCT/GB01/00831
§ 371 (c)(1),
(2), (4) Date: Nov. 7, 2002

(87) PCT Pub. No.: WO01/64125
PCT Pub. Date: Sep. 7, 2001

(65) Prior Publication Data
US 2003/0170591 A1 Sep. 11, 2003

(30) Foreign Application Priority Data
Feb. 29, 2000 (GB) ............................................. 0004636
Dec. 7, 2000 (GB) ............................................. 0029818

(51) Int. Cl.$^7$ ................................................ A61C 5/08
(52) U.S. Cl. ...................................... 433/220; 433/174
(58) Field of Search ............................ 606/61; 433/219, 433/220, 221, 75, 76, 174

(56) References Cited

U.S. PATENT DOCUMENTS

| | | |
|---|---|---|
| 4,693,644 A | 9/1987 | Takahashi |
| 5,118,294 A | 6/1992 | Kurer |
| 5,161,973 A | 11/1992 | Johnson |
| 5,282,747 A | 2/1994 | Nordin |
| 5,453,010 A | 9/1995 | Klein |

FOREIGN PATENT DOCUMENTS

| | | | |
|---|---|---|---|
| DE | 29700604 U | | 7/1997 |
| EP | 0 336 082 A | | 11/1989 |

Primary Examiner—Cary E. O'Connor
Assistant Examiner—Candice C. Stokes
(74) Attorney, Agent, or Firm—Hollander Law Firm, P.L.C.

(57) ABSTRACT

A pilot bore is cut into bone tissue; a post is fixed in the bore, and an elongate enlarged region is formed at the top end of the bore using a tubular cutter which is guided on the post. The elongate enlarged region can be accurately cut even with a hand drill due to the guidance provided by the post. The cutter may have holes or channels for circulation of cooling/lubricating liquid, and a swarf-removing slot may be provided. When the technique is used in dentistry for replacement of a tooth crown, a tubular support element is fixed around the post in the bore enlargement.

26 Claims, 7 Drawing Sheets

GUIDE POST FOR TREPHINE

This application is a 371 national stage application of PCT/GB01/00831 filed Feb. 27, 2001, which claims priority of United Kingdom application no. 0004636.7 filed Feb. 29, 2000, and United Kingdom application no. 0029818.2 filed Dec. 7, 2000.

TECHNICAL FIELD

This invention relates to the cutting of bores particularly in dental, oral or orthopaedic surgery and is particularly although not exclusively concerned with apparatus for use in dentistry to secure and support a crown post and superstructure to a residual tooth understructure—the remaining tooth root.

BACKGROUND ART

When cutting bores in tooth roots and in bone for location of inserted posts, pins, screws and implants in dental surgery and also in oral or orthopaedic surgery problems due to inaccuracy of the resulting diameter can arise especially where access is limited.

For secure location of the inserted pin or post it is necessary or at least desirable for the receiving bore to be cut with dimensions precisely matched to those of the pin, post or screw. However, in conditions of limited access, such as is the case where a bore is to be cut in a tooth root or jaw bone, it may be necessary for the bore to be cut with a hand drill or other manually controlled device whereby some degree of lateral movement and consequent unwanted enlargement of the bore may be inevitable.

More specifically, in the context of dental surgery an artificial crown can be fitted onto a sound tooth root by cementing a post into a bore in the root and then fixing the crown onto a projecting portion of the post.

Where the residual root and tooth structure extends above the gum this on its own or supported by the post can ensure long term, secure attachment between the post and the root. However, when the residual root structure terminates at or below the gum it can be more difficult to prevent loosening of the post in use.

With the aim of improving security of fixing it is well known to drill a bore in the root structure and to use a matching post which is cemented into the bore.

However, the diameter of the drilled bore tends to become enlarged over the diameter of the drill or reamer whereby a post having the same diameter as the drill bit tends to be too small in the bore i.e. fit badly and hence loosen in use. When a threaded bore and post have been applied this is particularly problematical since the post with attached crown may not be readily removable for re-cementing without breaking and removing the crown in so far as the crown has an irregular lower surface which mates with the top surface of the root structure thereby resisting unscrewing of the post.

Loosening of the post within the bore tends to occur more readily when the upper (coronal) regions of the root structure are over-reamed. This is common, and the fit tends to remain closer at the bottom (apical) end of the bore. This can encourage pivotal movement of the post under the action of transverse forces about a fulcrum (where it fits) and this can give rise to the generation of large, destructive forces to the root structure as well as the cementing medium.

It is known to use a post which is enlarged in its upper (coronal) end portion. This helps to avoid or limit damage by the fulcrum effect but it is difficult for a dentist using hand tools to form accurately the required shaped bore to receive and securely locate the special post profile.

A further problem in the cutting of bores is that heat is generated during the cutting operation and there is the problem of ensuring adequate removal or dissipation of this to prevent damage being caused to adjacent root material or tissue.

DISCLOSURE OF INVENTION

One object of the present invention is to provide an improved means of achieving secure location of a pin or post in a cut bore in dental, oral and orthopaedic surgery.

A further object is to provide an improved means of achieving secure crown post anchoring which can be implemented by a technique which is simple and convenient to perform particularly by a dentist using commonly available tools and instruments.

A yet further object of the present invention is to provide improved apparatus for use in cutting accurate bores in oral or orthopaedic surgery to avoid or minimise adverse effects from heat produced during the cutting procedure.

According to one aspect of the present invention therefore there is provided a method for surgically cutting a bore for location of an insert in bone tissue comprising the steps of: cutting a pilot bore in the bone tissue from a surface thereof, locating a guide post in the bore, and forming an enlarged region around the pilot bore with a tubular cutter known as a trephine, the tubular cutter being located co-axially around and in contact with the said guide post so as to be longitudinally guided thereby.

With this arrangement an accurate bore can be cut into which an insert can be fitted in a secure and stable manner.

The mode of cutting the bore is such that a bore of desired dimensions can be cut with great precision in a particularly simple and convenient manner using a technique which can be readily performed by a dentist or surgeon with instrumentation present in many dental surgeries and operating theatres. Consequently, the technique can be applicable in restorative dentistry and also may find utility in orthopaedic surgery e.g. in the attachment of prosthesis which are implants or reinforcements to bones, in the joining of bone structures, or for other purposes.

The simplicity of the technique arises from the use of a tubular cutter or trephine, which is guided on and by the guide post.

Preferably the guide post is located in the pilot bore such that an upper end portion of the guide post projects upwardly above the said surface. This facilitates initial guidance of the cutter by the post and subsequently the projecting end portion may be cut or broken away or left in position as desired. It may alternatively be possible to remove the post after it has served its purpose of guiding the cutter.

The tubular cutter may be used to cut any desired length of enlargement relative to the length of the post within the pilot bore. Thus, the enlargement may be a minor proportion of the length of the pilot bore, or a larger proportion, or even the entire length of the pilot bore.

Preferably, the guide post and tubular cutter are selected so the post has a substantially constant external diameter, at least for a major proportion of its length, and the tubular cutter has a constant internal diameter which is essentially the same as the constant external diameter of the guide post to give a close fit whilst permitting axial sliding and cutting rotation.

The post may have a smooth outer surface or may be configured to facilitate secure location in the pilot bore as for example by provision of an external screw thread or other projecting conformation to aid penetration or fixing or retention within the bore. Where a threaded post is used, the bore may be provided with an internal screw thread e.g. by use of a tapping device, prior to insertion of the guide post. It may also be self-tapping.

In order to facilitate removal of heat during cutting of the enlargement, provision may be made for circulation of cooling or lubricating liquid, such as water or saline, around the post in situ. Thus, for example, the post may have longitudinal grooves or channels in its outer surface, or the post may be tubular with an internal passageway and one or more apertures may be provided through a side wall of the tubular post in communication with the internal passageway.

The guide post may possess a tapered leading end, to assist in its insertion into the pilot bore.

The post may be formed as a metal or metal alloy pin, or a carbon fibre reinforced resin structure or any other suitable device.

With regard to the tubular cutter, this may be formed with teeth or other cutting or milling conformation such as diamonds on its leading end, and there may be a drive connection conformation, such as a pair of diametrically opposed outer longitudinal slots, possibly two pairs placed at rights angles to each other on its trailing end for drive connection to a rotary hand drill or other power tool. Alternatively or additionally there may be a friction fit or latch lock drive connection, or simply be engaged by a chuck.

Preferably the tubular cutter is provided with a configuration for releasing and removing swarf or cutting debris. In a particularly preferred embodiment the cutter has at least one longitudinal channel or through slot in its outer surface. This may run straight or may be curved preferably helically. Most preferably there is a through slot extending from or near the leading end of the cutter over a major part of the length of the cutter to a position close to or at a trailing end of the cutter. This slot may communicate with a groove or channel over the end portion from the slot to the trailing end.

The tubular cutter may be formed from metal or metallic alloy, (carbon fibre reinforced resin) or any other suitable material.

The invention also provides apparatus for use in performing the above method.

Thus, and in accordance with the second aspect of the invention there is provided cutting apparatus for use in the cutting of an enlarged bore in bone tissue comprising a drill cutter with which to form a pilot bore, an optional tap to produce a thread in the pilot bore if required, a guide post for insertion into and secure location within the pilot bore, and a tubular drill cutter which fits co-axially in close fit around the guide post so as to be rotatable and axially slideable relative thereto.

In accordance with a third aspect of the invention there is provided a tubular cutter for use with the aforementioned apparatus, said cutter having a cutting configuration at its leading end, and a drive connection conformation at its trailing end. The drive connection conformation may be as described above.

The cutter tube may also be provided with a swarf releasing and/or removing configuration as described above.

Further, the tube may be provided with a configuration for circulation of a cooling and/or lubricating fluid as described above.

Other features of the tubular cutter and post may also be as described above.

As mentioned, the invention is particularly suitable for use in restorative dentistry.

Thus, and in accordance with a fourth aspect of the invention there is provided a method for providing anchoring for attachment of a crown or dental superstructure to a residual tooth understructure (root) comprising the steps of: fixing a post within a bore in the root so that an upper end region of the post projects upwardly above a top end (coronal surface) of the bore, forming an enlarged coronal region of the bore with a tubular cutter with the cutter located co-axially around the projecting portion of the post, and fixing a support element around the post within the enlarged coronal region of the bore.

With this arrangement, the support element can act as a fulcrum stabilizer to resist loosening and damaging pivotal movement of the post under the action of transverse forces because it will fit precisely round the post and into the root. The mode of cutting the bore enlargement is such that a bore of desired dimensions can be cut with great precision in a particularly simple and convenient manner which can be readily performed by a dentist using instrumentation present in many dental surgeries. As with the above first embodiment of the invention, this is a consequence of the use of a tubular cutter or trephine, which is guided on and by the projecting end region of the post. The support element can be specially designed to fit precisely into the enlarged bore and around the post.

In furtherance of this, and as with the first embodiment of the invention, the post and cutter are preferably selected so that the post has a constant external diameter at least in its coronal region and over the adjacent region corresponding to the coronal portion of the bore, and the tubular cutter has a constant internal diameter which is substantially the same as the constant external diameter of the post to give a close fit whilst permitting axial sliding and cutting rotation.

The post may be of constant external diameter over all or at least a major part of its length and may be straight-edged as viewed in longitudinal cross-section throughout that part of the post which is of constant external diameter. Other arrangements are however also possible and if desired the post may have parts of differing diameters and/or may have an external screw thread or other projecting conformation to aid penetration or fixing or retention within the bore.

The bore may be precut and the post may be fixed within this wholly by cement or adhesive. Alternatively or additionally it may be fixed within the pre-cut bore by interlocking configurations such as screw threads. It is also possible to use the post as a self-tapping reamer or cutter, particularly having an external screw thread, whereby the post is drilled into the understructure to form the bore and is then after cementing, left in position as the anchoring post.

The post may be formed from any suitable material and thus may be formed as a metal or metal alloy pin, or a carbon fiber reinforced resin structure or the like.

With regard to the tubular cutter, as with the first aspect of the invention this may be formed with teeth or other cutting or milling conformation on its leading end, and there may be a drive connection conformation, such as a pair of diametrically opposed outer longitudinal slots, possibly two pairs placed at right angles to each other on its trailing end for drive connection to a rotary hand drill or other power tool. There may be a friction fit or latch lock drive connection.

After cutting the bore enlargement the tubular cutter may be disengaged from the projecting end region of the post to be replaced by the support element which may be of the form of a tube which fits securely in coaxial disposition around the post within the enlarged bore and preferably also projecting upwardly therefrom. This tube may be formed from metal or metallic alloys, carbon fiber reinforced resin or any other suitable material.

It is also possible to leave the tubular cutter in situ after cutting the bore enlargement whereby the cutter then functions as the support element.

The tubular support element may be straight sided in longitudinal cross-section so as to fit in smooth sliding relationship with regard to the post and the enlarged bore. However it is also possible to have interfitting projecting conformations, such as screw threads between the support element and the post and/or the enlarged bore.

The tubular support element may be furnished with a projecting flange. This may fit into a cavity prepared into the coronal surface (root face) of the remaining tooth understructure (root) by means of a jig guided tubular root facer. The cavity can be precision prepared and, the tubular root facer can be guided on the projecting upper end region of the post in like manner to the guiding of the enlarged bore trephine. The flange may be smoothly engaged or screwed or otherwise interfitted with the post on its inner diameter and with the precision recess cut round the post with its under and outer surface. This may also be furnished with self tapping threads.

The tubular root facer may be used additionally to the tubular cutter used to cut the bore enlargement. Alternatively, these may be combined in that for example, the tubular cutter may have a peripheral collar above its bottom end which is configured to act as the root facer.

After fixing of the post, cutting of the enlarged bore, and any root face recess cutting, followed by fixing of the support element, the crown or other dental superstructure can then be fixed e.g. by cement, composite resin or adhesive or a combination of these to the projecting upper end region of the post. This fixing may occur directly onto the post or if desired additionally or alternatively onto the support element and/or the flange-shaped structure around the post. In this case a second core-retaining flange could be provided on the outer surface of the support element.

Prior to such fixing of the superstructure it may first be necessary or desirable to cut away part of the projecting upper end region of the post and/or part of the support element or tubular cutter where this is left in situ. In the latter respect the length of post required for guidance of the cutter may be greater than that required for fixing of the superstructure.

The invention also provides apparatus for use in performing the above method. Thus, and in accordance with a fifth aspect of the present invention there is provided dental anchoring apparatus for use in fixing a dental superstructure to a residual tooth understructure comprising a post for fixing within a bore in the understructure so that an upper end region of the post projects upwardly above a top end of the bore, a tubular cutter which fits coaxially in close fit around said upper end region and a lower adjacent region of the post so as to be rotatable and axially slidable relative thereto, and a support element adapted to fit closely around said lower adjacent region of the post. The support element may be a tube and may be separate from or may be defined by part of the tubular cutter. The support element may incorporate or be used separately with a flange-shaped upper end structure to fit around the post extending transversely beyond the support element. The outer surface of the tube may be of circular cross-section, or alternatively may be hexagonal or octagonal if this increases resistance to transverse forces.

The features of the first, second and third aspects of the invention may be utilised in the fourth and fifth aspects and vice versa as appropriate.

BRIEF DESCRIPTION OF DRAWINGS

The invention will now be described further by way of example only and with reference to the accompanying drawings in which.

BEST MODE OF CARRYING OUT THE INVENTION

Figure 1:
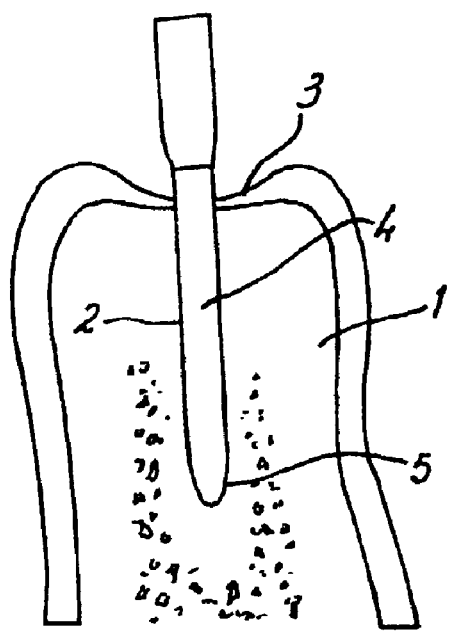
FIG. 1 is a diagrammatic cross-section showing a bone structure with a reamer cutting a pilot bore in accordance with one embodiment of the invention.
Figure 2:
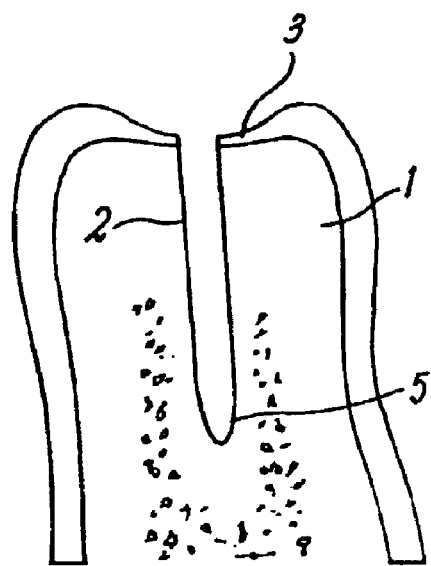
FIG. 2 is a view similar to FIG. 1 showing the cut bore.
Figure 3:
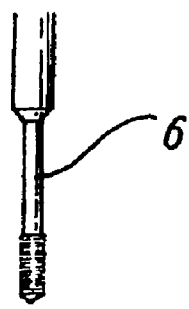
FIG. 3 is a side view of a tap.
Figure 4:
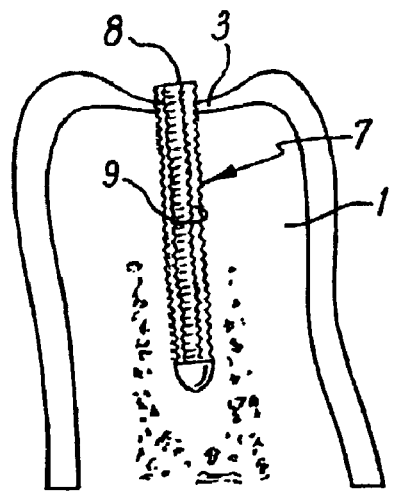
FIG. 4 is a view similar to FIG. 1 showing a threaded and grooved post inserted into the pilot bore.
Figure 5:
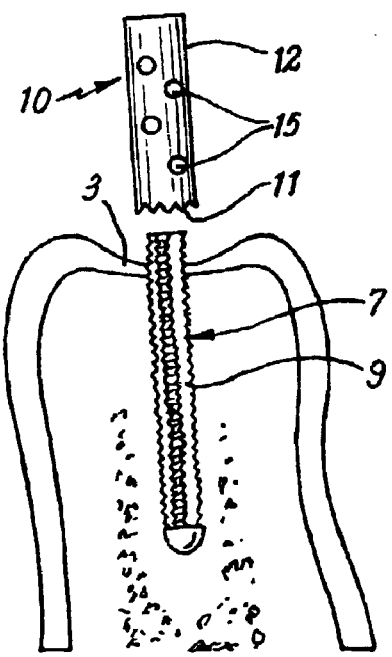
FIG. 5 is a view similar to FIG. 4 showing a tubular cutter.
Figure 7:
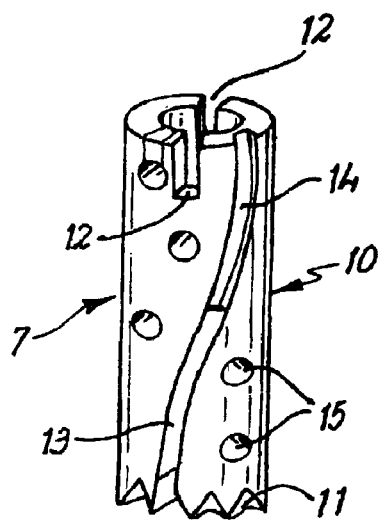
FIG. 7 is a diagrammatic perspective view of the tubular cutter to a larger scale.
Figure 6:
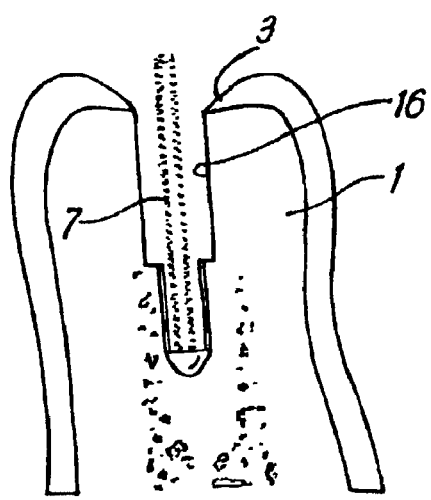
FIG. 6 is a view similar to FIG. 4 showing a cut bore enlargement.

FIG. 1 shows a bone structure 1 having a bore 2 which is cut from a top surface 3 using a reamer 4 fitted to a powered hand drill. The bore is shown tapered at its bottom end 5. The bore may be cut in conventional manner so as to have an internal screw thread. This may be achieved using a tap 6 which may be used after the bore-cutting reamer 4.

A post 7 is inserted into the bore 2. As shown the post is a metal, metal alloy or carbon fibre pin having a substantially constant diameter, with an external threaded surface, and flat or rounded ends. The post 7 is screwed into the threaded bore 2 and may be cemented in position.

The post 7 is of a length greater than the bore 2 so that, when fully screwed in, an upper end portion 8 of the post 7 projects freely above the face 3 of the bone structure 1.

As shown in the drawings, the post 7 has four longitudinal straight grooves or channels 9 in its outer surface. These grooves 9 are equally spaced around the periphery of the post 7 and extend throughout the entire length of the post 7. As described hereinafter these grooves 9 are to receive cooling water or saline and to allow swarf to be expelled.

A tubular cutter 10, or trephine is then fitted to the end of a powered hand drill and is located coaxially on the projecting end region 8 of the post 7.

As shown, the trephine 10 comprises a tube having internal and external diameters which are uniform along the length of the tube. At its leading end the tube has peripheral cutting teeth 11 or has a diamond covered or tungsten carbide coated edge around its periphery. At its trailing end the tube has diametrically opposed longitudinal slots 12 in its exterior surface for driveable connection with a chuck of the drill.

Beginning at its leading end the trephine 10 has at least one through slot or slit 13 which extends through at least half the length of the tube and runs along a sinuous or curved or helical path. The slot 13 terminates at a position spaced from the trailing end of the tube. Between this position and the trailing end, there is a groove 14 which links continuously with the slot 13, such groove extending only partially through the wall of the tube from its outer surface.

In addition the tubular cutter possesses cross-drilled holes 15 extending at spaced positions around the periphery of the tube through the wall of the tube. As described hereinafter these holes are to allow passage of cooling water or saline, and the slot and groove 13, 14 are to allow removal or swarf.

The trephine 10 is formed from stainless steel or other suitable alloy and the diameter of its inner periphery is essentially the same as the external diameter of the post 7 so that the trephine 10 fits slideably on the post 7 so as to be rotatably and axially movable relative to the post with essentially no play therebetween.

During cutting rotation of the trephine cooling water or saline is fed to the top end of the post 7 so as to flow down the channels 9 in the post 7 and through the holes 15 in the trephine 10. This may be achieved by a pressurised liquid feed to a hand held outlet discharging onto the face of the post 7. Alternatively there may be a feed tube attached to the drill so as to discharge directly into the interior of the tube 10 above the top end of the post 7.

As the trephine 10 rotates it cuts an enlargement 16 in the bone structure around the post 7. The drill is advanced so that the enlargement extends to at least 50% of the post's length as indicated in the drawings. This enlargement 16 can be cut with great precision in so far as the trephine 10 is accurately guided on the post 7. The cutting of the bore enlargement 16 can be achieved in a particularly simple manner by an oral or orthopaedic surgeon despite the use of hand held instruments.

During the cutting operation, material removed from the bone structure by the trephine 10 is displaced through and along the slot (or slots) 13 and associated groove (or grooves) 14 out away from the bore 3.

After cutting of the bore enlargement 16, the trephine 10 may be removed, providing a precise aperture for the location of a tubular insert around the post 7. The insert may be cemented in position and may be used for attachment to a prosthesis or adjacent bone structure as desired. If desired and where possible the post 7 may be removed or cut back prior to introduction of the insert.

Alternatively, the cutter 7 can remain in situ so as to act itself as the insert.

Figure 8:
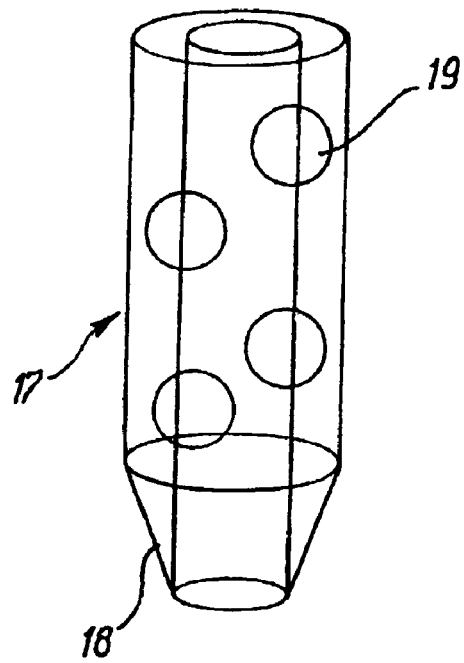
FIG. 8 is an enlarged view of an alternative guide post.
Figure 9:
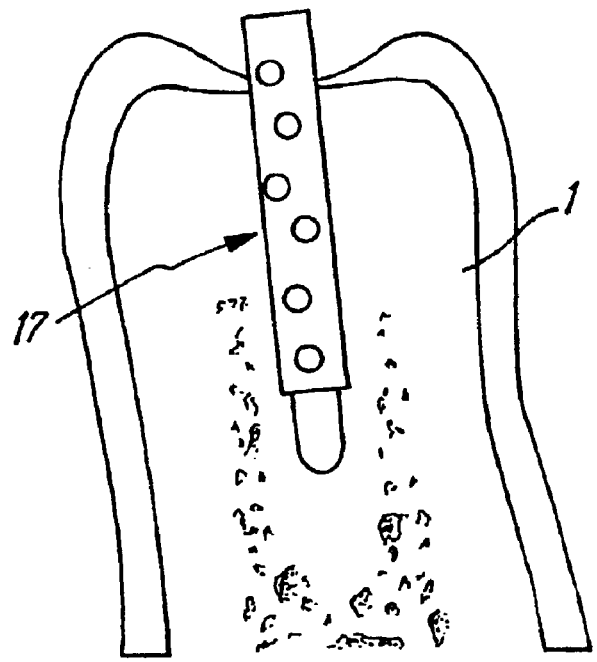
FIG. 9 is a view similar to FIG. 4 showing a post similar to that of FIG. 8.

As shown in FIGS. 8 & 9, in a modified embodiment the guide post 17 comprises a tube having internal and external diameters which are uniform along its length, except for the leading end region 18 where the tube is tapered externally to facilitate insertion into a drilled pilot bore. With this embodiment the pilot bore and the exterior of the post are not threaded; the post 17 is pushed into the bore and cemented in position.

The post 17 has cross-drilled holes 19 spaced around its periphery extending completely through the outer wall of the tubular post 17.

Once in position, the post 17 is used with a trephine 10 in the same manner as the first described embodiment. Cooling liquid is directed through the cross-drilled holes 19 for cooling purposes by admission to the interior of the post 17.

Figure 10A:
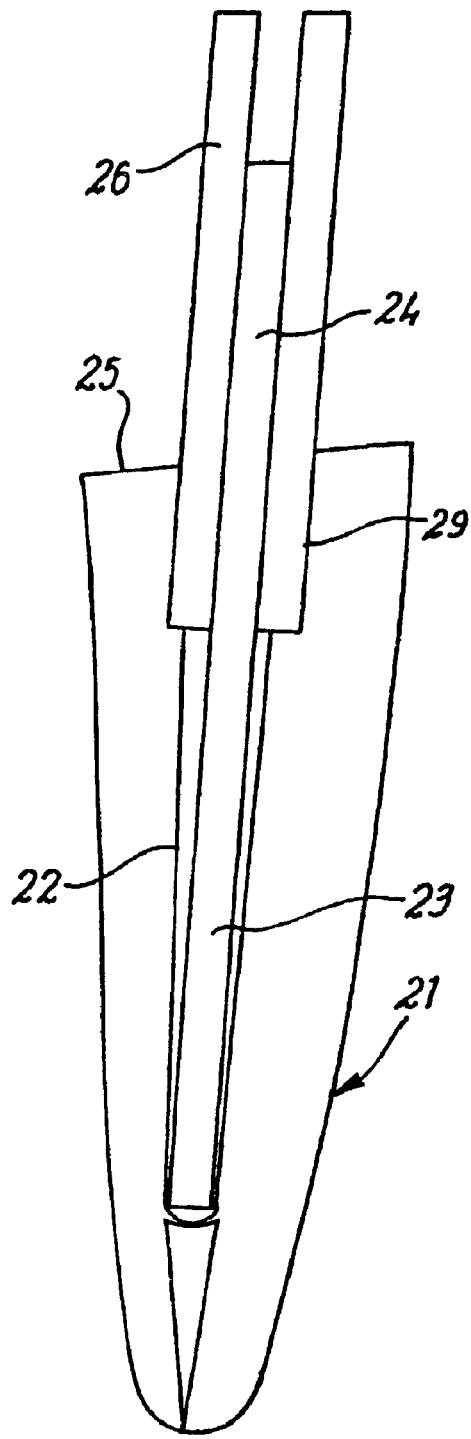
FIG. 10a is a diagrammatic cross-section showing a tooth root with an inserted post and cutter in accordance with one aspect of the invention.
Figure 10B:
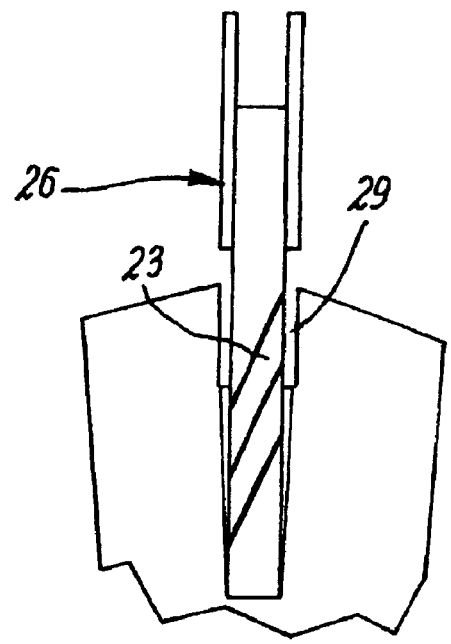
FIGS. 10b & 10c show stages in the cutting of an enlarged bore and insertion of a support element.
Figure 10C:
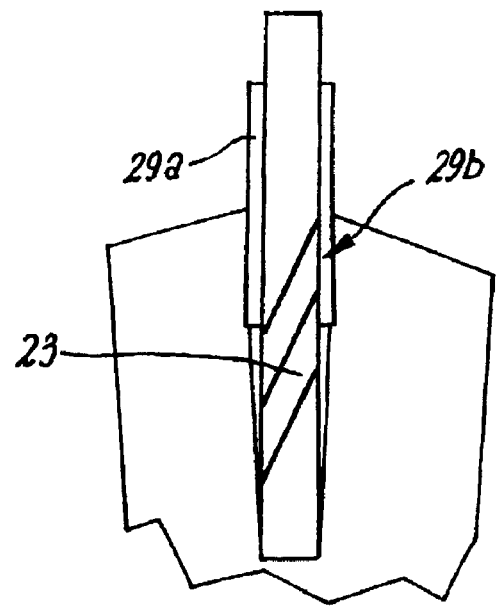

Referring to FIGS. 10a–10c, these show a tooth root 21 having a bore 22 which may be cut in conventional manner by a dentist using a reamer powered by a powered hand drill. The bore is shown tapered as tends to be but may not always be the case in practice notwithstanding the use of a parallel sided reamer.

A post 23 is cemented into the bore. As shown the post is a metal, metal alloy or carbon fiber pin having a constant diameter, straight sides and flat or rounded ends. The post 23 is of a length substantially greater than the bore length so that an upper end region 24 of the post 23 projects freely above a top end (coronal) face 25 of the root 21.

The cement extends within the bore 22 around the post 23 between the post 23 and the sides of the tooth bore 22. The post 23 is held in position and the cement is allowed to set completely.

A tubular cutter 26, or trephine, is then fitted to the end of a powered drill and is located on the projecting end region 24 of the post 23.

Figure 11:
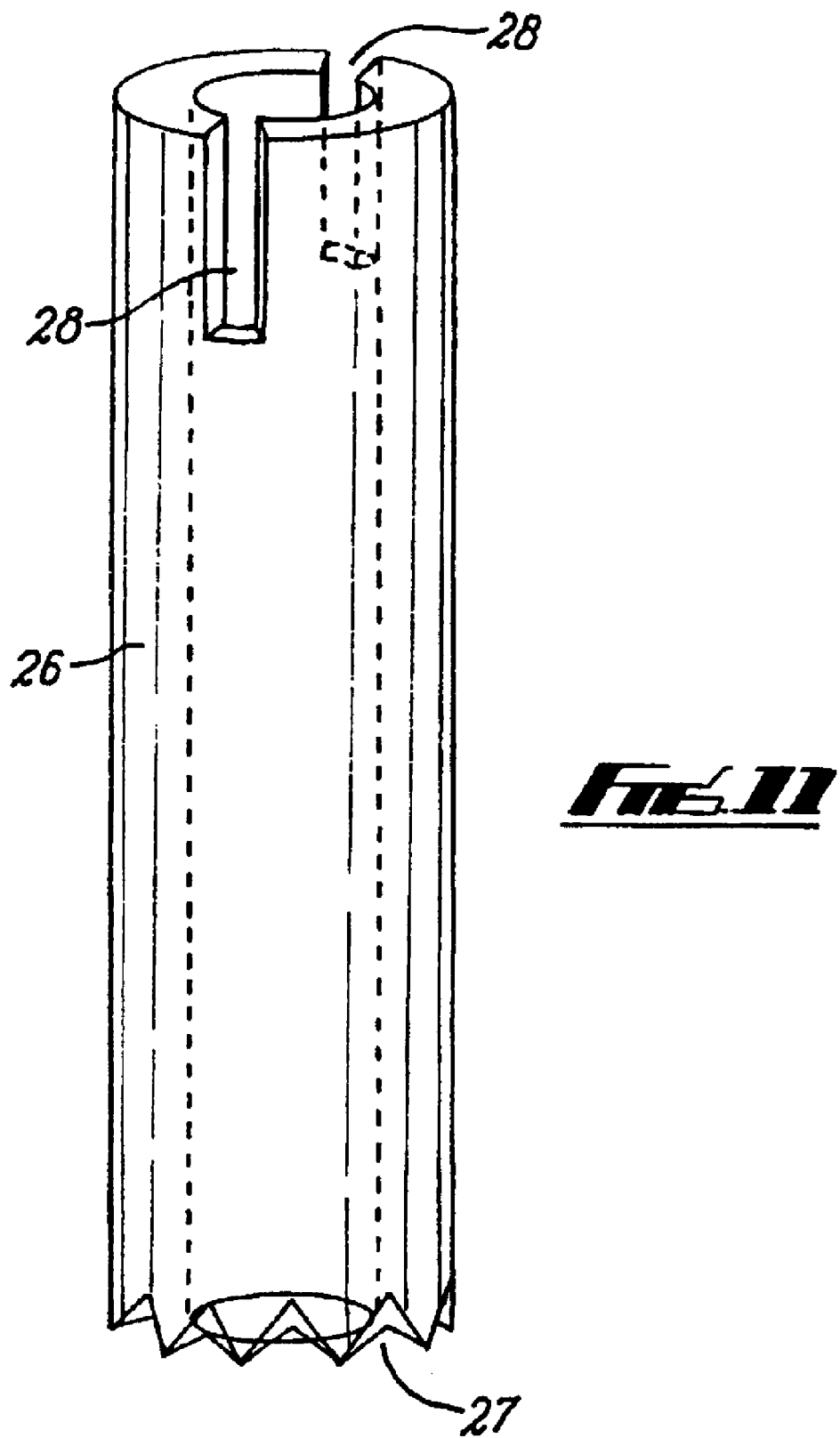
FIG. 11 is a perspective view of the cutter of FIG. 10.

As shown in FIG. 11, the trephine 26 comprises a tube having constant internal and external diameters. At its leading end the tube has cutting teeth or diamond covered or tungsten carbide leading end 27 around its periphery. At its trailing end there are diametrically opposed longitudinal slots 28 in its exterior surface for driveable connection with a chuck of the drill.

The trephine 26 is formed from stainless steel or other suitable alloy and the diameter of its inner periphery is substantially the same as the external diameter of the post 23 so that the trephine 26 fits slideably on the post 23 so as to be rotatably and axially movable relative to the post with essentially no play there between.

The trephine 26 is used to cut an enlargement 29 to the upper end region of the bore 22 as indicated in the drawings. This enlargement 29 can be cut with great precision in so far as the trephine 26 is accurately guided on the cemented post 23. The cutting of the bore enlargement 29 can be achieved in a particularly simple and convenient manner by the dentist.

After cutting of the bore enlargement 29, the trephine 26 can be removed from the post at 24.

A support element 29a, or fulcrum stabilizer is now fitted into the enlarged bore 29 around the post 23 extending throughout the longitudinal extent of the bore enlargement 29 and if desired projecting upwardly beyond the root face 25 (FIG. 10c).

The support element 29a may comprise a stainless steel tube which is dimensioned so that its internal and external diameters are essentially identical with those of the trephine 26 whereby the support element 29a fits closely between the post 23 and the inner surface of the bore enlargement 29.

If desired, instead of using a separate tube, the trephine itself may be placed in situ i.e. re-inserted, to act as the support element. The driveable end would then be cut off at a suitable point. Its precision fit into the bore would be assured.

The support element 29a is then cemented in position (at 29b) and the cement is allowed to set completely.

At this stage, the upper end region 24 of the post 23, and possibly also an upper part of the support element 29a, especially if the trephine 26 is used as the support element 29a, may extend appreciably above the root face 25. These parts may therefore be cut down to give projecting lengths suitable for attachment of a crown.

The attachment of the crown is then facilitated by well known means. Composite resin is commonly used to build up the cut down projecting end region 24 of the post 23, and possibly also the support element 29a, so that the crown is securely connected, positioned and engaged with the root face 25.

With this arrangement, the post 23 and support element 29a can be securely fixed in the root in a particularly simple and convenient manner. When fixed, it will be seen that the support element 29a acts as a fulcrum stabiliser or post stabiliser at the upper end of the tooth bore to resist loosening and damage to the tooth root caused by applied transverse forces.

Figure 12A:
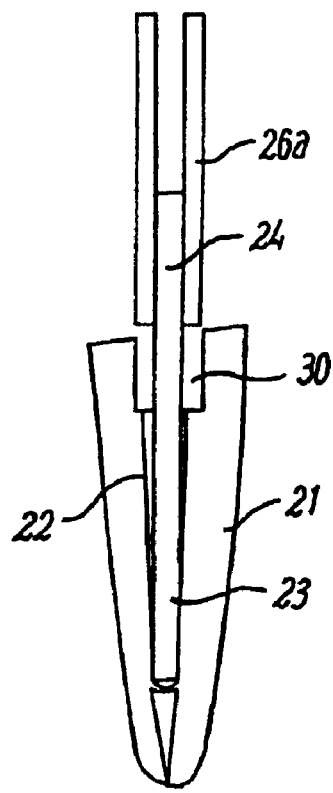
FIGS. 12a–c are views similar to FIG. 10 showing a further embodiment using two jig guided root facers.

The embodiment of FIG. 12 is similar to that of FIG. 10 and the same reference numerals are used for corresponding parts. However, after the post 23 has been cemented in the bore 22, two bore enlargements 30, 31 are cut using two trephines 26a, 26b, instead of the single bore 29 of FIG. 10, these trephines 26a, 26b being accurately guided on the cemented post 23.

The first bore 30 is cut with a trephine 26a (FIG. 12a) of similar structure to that shown in FIG. 11. This bore 30 may be like the bore 29 and may be wider than the top end of the bore 22.

Figure 12B:
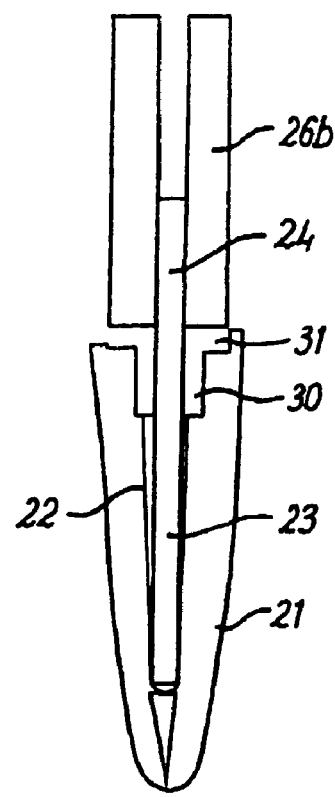

The second bore or preparation 31 is of the nature of a shallow disc-shaped recess which is cut into the root face using a larger trephine 26b (FIG. 12b).

Figure 12C:
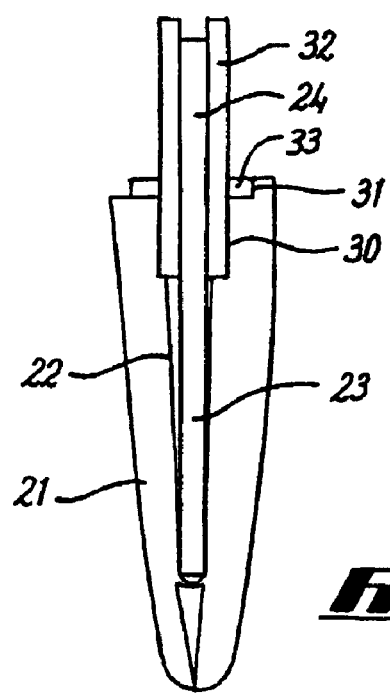

The support element accurately fitted into the cut bores 30, 31 may be constructed as an integral structure with two parts: a tubular part 32 for the bore 30 and an integral annular root face contact flange 33 for the bore 31 (FIG. 12C). Alternatively the tubular part 32 and the root face contact flange 33 may be formed as separate parts.

The annular disc root face contact flange 33 in the top bore 31 further promotes fulcrum stabilization and stress distribution along the length of the root. This is advantageous because it decreases the likelihood of root fracture resulting from transverse forces acting on the crown and hence on the post.

Figure 13:
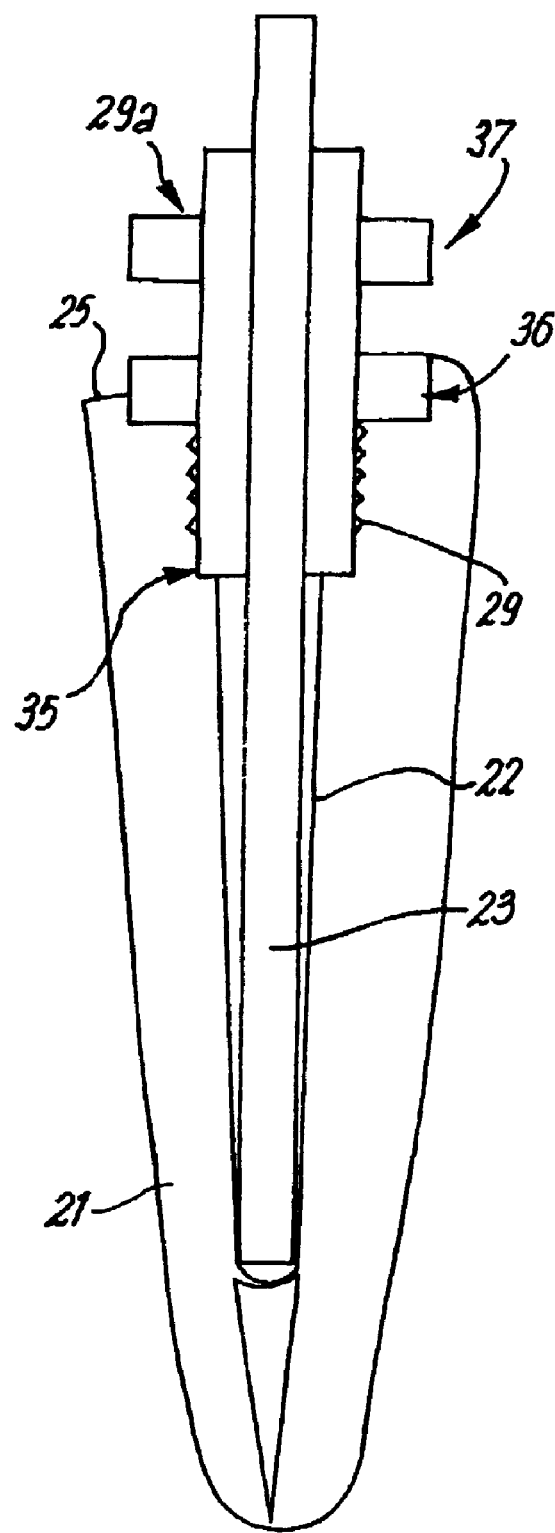
FIG. 13 is a view similar to FIG. 10 showing a further embodiment.

The embodiment of FIG. 13 is similar to that of FIG. 12, and the same reference numerals are used for corresponding parts. As described in accordance with FIG. 12, two bores 30, 31 are formed and into these there are fitted a tubular part 35 of the support element 29a, and a root face contact flange 36 which may be integral with or separate to the tubular part 35. Additionally a core retaining flange 37 is fixed around the tubular part 35. This flange 37 provides a key for the usual composite resin core for the crown. The flange 37 may be integral with or separate to and fixed on the tubular part 35.

With the embodiments of FIGS. 10–13, if desired, the post 3 may be threaded and screwed into the bore. Also the support element may be screwed onto the post 3. The trephine 26 may be as described in connection with the embodiments of FIGS. 1–9.

It is of course to be understood that the invention is not intended to be restricted to the details of the above embodiments which are described by way of example only.

Thus, for example, although reference is made herein to the use of hand drills the procedure of the invention can also be applied to other apparatus and techniques for cutting bores.

What is claimed is:

1. A method for surgically cutting a bore for location of an insert in bone tissue comprising the steps of:

cutting a pilot bore in the bone tissue from a surface thereof, locating a guide post in the bore, and forming an elongate enlarged region around the pilot bore with an elongate tubular cutter, the elongate tubular cutter being located co-axially around and in contact with the guide post so as to be longitudinally guided thereby.

2. A method according to claim 1 wherein the guide post is located in the pilot bore such that an upper end portion of the guide post projects upwardly above the surface.

3. A method according to claim 1, wherein the elongate enlarged region extends to at least 50% of the length of the guide post.

4. Dental anchoring apparatus for use in fixing a dental superstructure to a residual tooth understructure comprising:

a drill cutter for forming a pilot bore, a post for fixing within the bore in the understructure so that an upper end region of the post projects upwardly above a top end of the bore, an elongate tubular cutter which fits coaxially in close fit around said upper end region and a lower adjacent region of the post so as to be rotatable and axially slidable relative thereto, for cutting an elongate enlarged region of the bore, and a support element adapted to fit precisely around said lower adjacent region of the post, wherein the support element comprises a tube a separate from the elongate tubular cutter.

5. Apparatus according to claim 4 wherein the guide post has a substantially constant external diameter at least for a major proportion of its length, and the elongate tubular cutter has a constant internal diameter which is essentially the same as the constant external diameter of the post.

6. Apparatus according to claim 4 wherein the guide post is a threaded post for engagement with an internal screw thread of the bore.

7. Apparatus according to claim 4 wherein the guide post has longitudinal grooves or channels (9) in its outer surface for circulation of liquid.

8. Apparatus according to claim 4 wherein the guide post is tubular with an internal passageway communicating with one or more side apertures for circulation of liquid.

9. Apparatus according to claim 4 wherein the guide post has a tapered leading end.

10. Apparatus according to claim 4 wherein the support element is provided with a projecting flange.

11. Apparatus according to claim 10 wherein a tubular root facer is provided for cutting a cavity in the coronal surface or root face to receive the projecting flange.

12. Apparatus according to claim 4 wherein the guide post is a threaded post for engagement with an internal screw thread of the bore.

13. Apparatus according to claim 4 wherein the guide post has longitudinal grooves or channels in its outer surface for circulation of liquid.

14. Apparatus according to claim 4, wherein the elongate enlarged region extends to at least 50% of the length of the guide post.

15. Apparatus according to claim 4, wherein the support element projects upwardly beyond a root face.

16. Apparatus according to claim 4 wherein the elongate tubular cutter has at least one longitudinal slot in its outer surface for removing swarf.

17. Apparatus according to claim 16 wherein the slot is helically curved.

18. Apparatus according to claim 16 wherein the slot extends from a leading end of the elongate tubular cutter over a major part of the length of the cutter to a position spaced from a trailing end of the cutter, a groove or channel being provided over the end portion from the slot to the trailing end.

19. A method for providing anchoring for attachment of a crown or dental superstructure to a residual tooth understructure or root comprising the steps of:

fixing a post within a bore in the root so that an upper end region of the post projects upwardly above a top end or coronal surface of the bore, forming an elongate enlarged coronal region of the bore with an elongate tubular cutter with the cutter located co-axially around the projecting portion of the post, and fixing a support element around the post within the elongate enlarged coronal region of the bore.

20. A method according to claim 19 wherein after cutting the bore enlargement, the tubular cutter is disengaged from the projecting end region of the post to be replaced by the support element.

21. A method according to claim 19 wherein after cutting the bore enlargement the elongate tubular cutter is left in situ to function as the support element.

22. A method according to claim 19, wherein the elongate enlarged region extends to at least 50% of the length of the guide post.

23. A method according to claim 19, wherein the support element projects upwardly beyond a root face.

24. Dental anchoring apparatus for use in fixing a dental superstructure to a residual tooth understructure, comprising:

a post for fixing within a bore in the understructure so that an upper end region of the post projects upwardly above a top end of the bore, an elongate tubular cutter which fits coaxially in close fit around the upper end region and a lower adjacent region of the post so as to be rotatable and axially slidable relative thereto, for cutting an elongate enlarged region of the bore, a tubular root facer for cutting a cavity in the coronal surface, and a support element adapted to fit closely around the lower adjacent region of the post, wherein the support element comprises a tube separate from the elongate tubular cutter.

25. An apparatus according to claim 24, wherein the tubular root facer is combined with the tubular cutter, the tubular cutter having a peripheral collar above its bottom end which is configured to act as the root facer.

26. Apparatus according to claim 24 wherein the support element is provided with a projecting flange and the cavity in the coronal surface or root face receives the projecting flange.

* * * * *